US012285257B2

(12) United States Patent
Jones et al.

(10) Patent No.: US 12,285,257 B2
(45) Date of Patent: Apr. 29, 2025

(54) WASTE DETECTION SYSTEM

(71) Applicant: C. R. Bard, Inc., Franklin Lakes, NJ (US)

(72) Inventors: Jill Walthall Jones, Avondale Estates, GA (US); Christopher K. Brooks, Lawrenceville, GA (US); David Xu, Cary, NC (US); Jason Jishen Cheng, Avondale Estates, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 548 days.

(21) Appl. No.: 17/556,883

(22) Filed: Dec. 20, 2021

(65) Prior Publication Data

US 2022/0192563 A1 Jun. 23, 2022

Related U.S. Application Data

(60) Provisional application No. 63/213,106, filed on Jun. 21, 2021, provisional application No. 63/128,644, filed on Dec. 21, 2020.

(51) Int. Cl.
| | |
|---|---|
| *A61F 13/15* | (2006.01) |
| *A61B 5/00* | (2006.01) |
| *A61B 5/20* | (2006.01) |
| *A61B 10/00* | (2006.01) |
| *A61F 5/451* | (2006.01) |
| *A61F 13/42* | (2006.01) |
| *G01N 33/48* | (2006.01) |

(52) U.S. Cl.
CPC ............ *A61B 5/207* (2013.01); *A61B 5/0077* (2013.01); *A61B 5/6892* (2013.01); *A61B 10/0038* (2013.01); *A61B 10/007* (2013.01); *A61F 5/451* (2013.01); *A61F 2013/15154* (2013.01); *A61F 2013/422* (2013.01); *G01N 33/48* (2013.01)

(58) Field of Classification Search
CPC ..... A61B 5/207; A61B 5/0077; A61B 10/007; A61F 5/41; A61F 2013/15154; A61F 2013/422; G08B 13/14; B08B 21/18; B08B 21/00; G01N 33/48
See application file for complete search history.

(56) References Cited

U.S. PATENT DOCUMENTS

| | | | |
|---|---|---|---|
| 6,203,496 B1 * | 3/2001 | Gael | G01N 33/528 |
| | | | 604/362 |
| 10,383,564 B2 | 8/2019 | Meek et al. | |
| 2004/0220538 A1 | 11/2004 | Panopoulos | |
| 2017/0265789 A1 * | 9/2017 | Naseri | A61B 5/14507 |

* cited by examiner

*Primary Examiner* — Jacqueline F Stephens
(74) *Attorney, Agent, or Firm* — Rutan & Tucker LLP

(57) ABSTRACT

Disclosed herein is a waste detection system. The waste detection system includes a pad configured to acquire a fluid sample excreted from a patient. The pad includes one or more layers and at least one microfluidic channel configured to receive therein the fluid sample. The waste detection system further includes an intake manifold in fluid communication with the at least one microfluidic channel, the intake manifold configured to receive the fluid sample, the intake manifold having one or more reagents configured to detect the presence of waste within the fluid sample excreted from the patient.

37 Claims, 11 Drawing Sheets

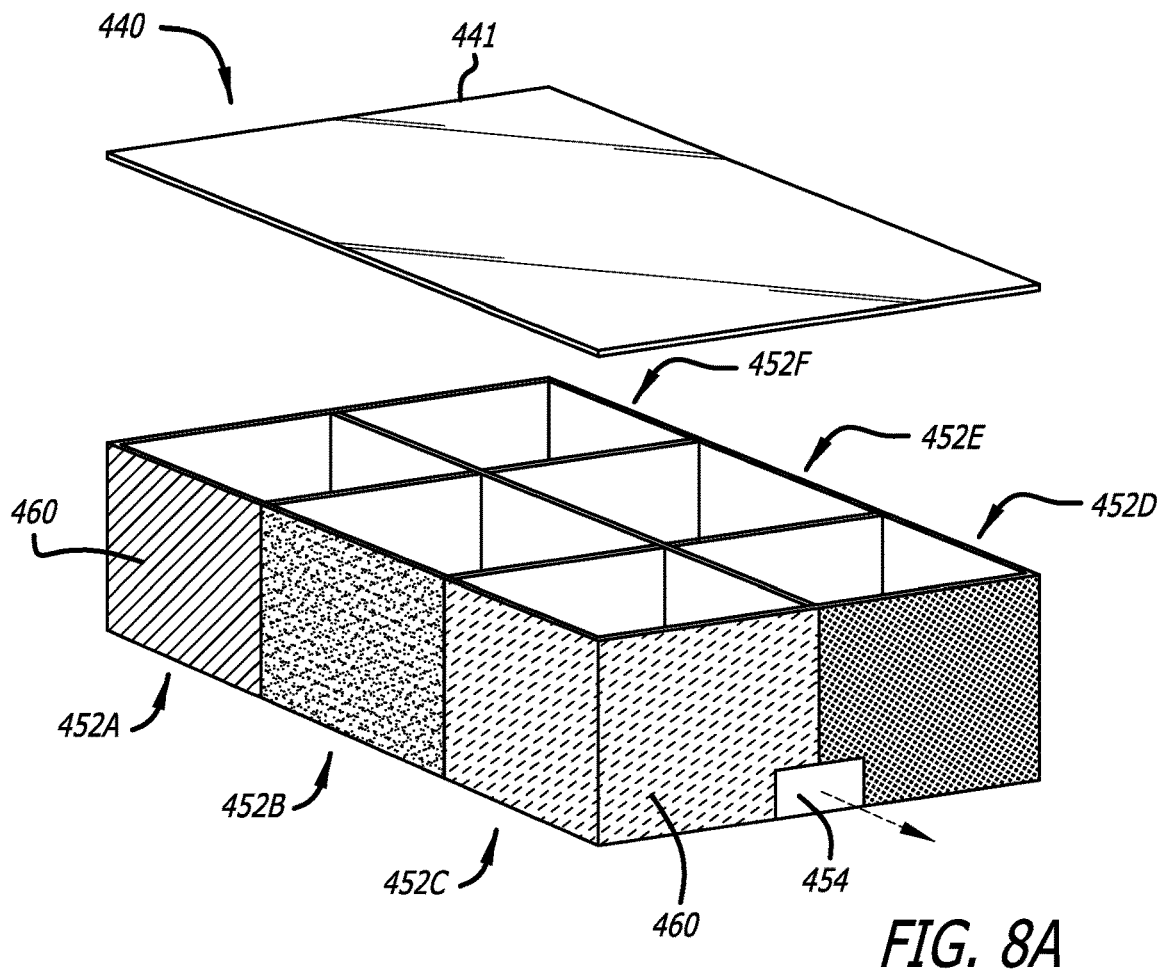
FIG. 8A
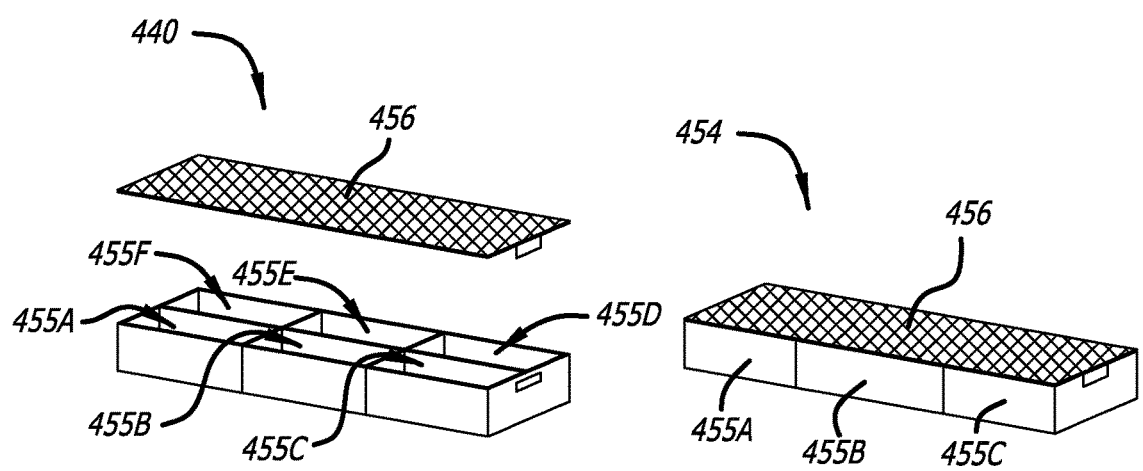
FIG. 8B
FIG. 8C

WASTE DETECTION SYSTEM

PRIORITY

This application claims the benefit of priority to U.S. Provisional Application No. 63/128,644, filed Dec. 21, 2020, and to U.S. Provisional Application No. 63/213,106, filed Jun. 21, 2021, each of which is incorporated by reference into this application.

BACKGROUND

Medical patients can lose their ability to control their bowel movements. Involuntary bowel movements for patients confined to a medical bed can lead to an increase in pressure ulcers, a breakdown of skin integrity and infection. To detect whether a bowel movement has occurred, caretakers of these patients most question the patient or visually detect whether a bowel movement has occurred. If a bowel movement has occurred, the caretaker must clean up the patient, dispose of any contaminated clothing or bedding, and dress the patient again. If the patient is wearing a diaper, the caretaker may have to remove the diaper for visual determination of a bowel movement occurrence. It would be beneficial to the patient and more efficient for the caretaker to be able to detect if a bowel movement has occurred without questioning the patient or visually inspecting the patient.

SUMMARY

Disclosed herein is a waste detection system. The waste detection system includes a pad configured to acquire a fluid sample excreted from a patient. The pad includes one or more layers and at least one microfluidic channel configured to receive therein the fluid sample. The waste detection system further includes an intake manifold in fluid communication with the at least one microfluidic channel, the intake manifold configured to receive the fluid sample, the intake manifold having one or more reagents configured to detect the presence of waste within the fluid sample excreted from the patient.

In some embodiments, the one or more layers includes a portion of the one or more layers having absorbent properties.

In some embodiments, the one or more layers includes a portion of the one or more layers having wicking properties.

In some embodiments, the one or more microfluidic channels are located within the portion having absorbent properties.

In some embodiments, the one or more microfluidic channels are located within the portion having wicking properties.

In some embodiments, the pad is placed under a lower abdominal region of a patient.

In some embodiments, the waste includes urine, stool, blood or *Clostridioides difficile*.

In some embodiments, the one or more microfluidic channels are coupled to the intake manifold at a proximal side or a distal side.

In some embodiments, the intake manifold includes one or more chambers configured to include the one or more reagents therein.

In some embodiments, the one or more chambers are configured in the shape of a cylinder, a rectangular prism, or an inverse cone.

In some embodiments, the intake manifold is detachably coupled to the pad.

In some embodiments, the pad is disposable.

In some embodiments, the intake manifold is disposable or reusable.

In some embodiments, the one or more reagents are in a solution form, a liquid form or a powder form.

In some embodiments, the intake manifold includes one or more hooks or one or more magnets configured to suspend the intake manifold from a medical bed.

Also disclosed herein is a method of detecting waste excreted from a patient. The method includes acquiring a fluid sample excreted from a patient on a pad, transferring the fluid sample from the pad to an intake manifold in fluid communication with the pad, detecting the presence of waste within the fluid sample, and indicating a bowel movement has occurred.

In some embodiments, acquiring the fluid sample excreted from the patient on the pad includes the pad being placed under a lower abdominal region of the patient.

In some embodiments, the waste includes urine, stool, blood, or *Clostridioides difficile*.

In some embodiments, acquiring includes wicking away the fluid sample from a patient using a wicking portion of the pad and absorbing the fluid sample into pad using an absorbing portion of the pad.

In some embodiments, transferring the fluid sample from the pad to the intake manifold includes using capillary action, gravity flow or negative pressure flow to transfer the fluid sample from the pad to the intake manifold.

In some embodiments, detecting includes using the one or more reagents in a chemical reaction or biochemical assay to detect the presence of waste.

In some embodiments, indicating a bowel movement has occurred includes the one or more reagents emitting a visible color or undergoing a visible color change within the intake manifold to indicate a bowel movement has occurred.

Also disclosed herein is a waste detection system. The waste detection system includes a pad configured to receive a fluid sample excreted from a patient, the pad being placed under a lower abdominal region of the patient, the pad having a proximal side, a distal side, one or more layers and at least one microfluidic channel configured to receive therein the fluid sample. The waste detection system further includes an intake manifold in fluid communication with the at least one microfluidic channel and configured to receive the fluid sample, the intake manifold including one or more reagents configured to detect the presence of waste within the fluid sample excreted from the patient. The waste detection system includes an analyzer configured to receive therein a portion of the intake manifold, the analyzer having a console in communication with a camera configured to detect one or more visible colors or visible color changes of the reagents within the intake manifold.

In some embodiments, the one or more reagents are configured to detect the presence of waste within the fluid sample by detecting one or more analytes within the fluid sample.

In some embodiments, detecting one or more analytes within the fluid sample includes the one or more reagents emitting a visible color or undergoing a visible color change.

In some embodiments, detecting one or more analytes within the fluid sample includes detecting one or more analytes when the one or more analytes are above a threshold.

In some embodiments, the one or more detected analytes include a panel of disease state specific analytes or treatment plan specific analytes.

In some embodiments, the one or more detected analytes include urine, stool, glucose, protein, or bacteria.

In some embodiments, the bacteria includes *Clostridium difficile*.

In some embodiments, the intake manifold includes one or more chambers configured to receive a portion of the fluid sample therein.

In some embodiments, each chamber includes the one or more reagents therein configured to detect different analytes within the fluid sample.

In some embodiments, each chamber includes the one or more reagents therein configured to detect the same analytes within the fluid sample.

In some embodiments, the one or more reagents are configured to emit a color or undergo a visible color change in proportion to the concentration of the detected analyte in the fluid sample.

In some embodiments, the intake manifold includes a removable wafer, the removable wafer having one or more wafer compartments in fluid communication with the one or more chambers, the wafer compartments configured to receive therein a portion of the fluid sample, the removable wafer including a wafer cover configured to seal therein the fluid sample.

In some embodiments, the analyzer is configured to receive the removable wafer therein.

In some embodiments, the console having one or more processors, an energy source, non-transitory computer readable medium, and a plurality of logic modules.

In some embodiments, the console is in communication with a docking station, a computing device, or an electronic medical record system.

In some embodiments, the plurality of logic modules, when executed by the processor are configured to perform operations including activating the analyzer including the camera, calibrating the analyzer including the camera, capturing one or more images of the intake manifold or the removable wafer, detecting one or more colors or color changes from the one or more images of the intake manifold or the removable wafer, correlating the one or more detected colors or color changes with a result value and time of day value, analyzing the result value, and transmitting the result value, the time of day value and the captured image to a computing device or an electronic medical record system.

In some embodiments, the analyzer is configured to detachably couple to the docking station.

In some embodiments, calibrating the analyzer includes calibrating the analyzer with a reference color pad.

In some embodiments, capturing one or more images of the intake manifold or the removable wafer includes the camera capturing the one or more images when the intake manifold or the removable wafer is coupled to the analyzer.

In some embodiments, the pad includes pad channels in fluid communication with the one or more microfluidic channels, the pad channels defined by absorbent material between wicking fiber.

In some embodiments, a portion of the wicking fiber or the entire wicking fiber is covered with a hydrophilic coating configured to create a hydrophilic gradient.

In some embodiments, each of the pad, the intake manifold and the removable wafer are disposable or reusable.

Also disclosed herein is a method of receiving and analyzing a fluid sample excreted from a patient for waste. The method includes configuring a waste detection system for collection of a fluid sample. The waste detection system includes a pad with one or more layers and one or more microfluidic channels configured to receive therein the fluid sample, the one or more microfluidic channels in fluid communication with an intake manifold having one or more reagents configured to detect one or more analytes within the fluid sample. The intake manifold further includes one or more chambers and a removable wafer configured to receive therein a portion of the fluid sample. The waste detection system further includes an analyzer having a console, the analyzer configured to receive therein a portion of the intake manifold and detect one or more visible colors or visible color changes of the reagents. The method further includes receiving the fluid sample excreted from the patient, transferring the fluid sample from the pad to the intake manifold, detecting the one or more analytes in the fluid sample within the intake manifold, and analyzing the detected one or more analytes and transmitting the results to a computing device or electronic medical record system.

In some embodiments, configuring the waste detection system for collection of a fluid sample includes placing the pad under a lower abdominal region of a patient and placing the intake manifold in fluid communication with the pad.

In some embodiments, receiving a fluid sample excreted from the patient includes the pad acquiring the fluid sample.

In some embodiments, receiving a fluid sample includes absorbing the fluid sample into the pad.

In some embodiments, transferring the fluid sample from the pad to the intake manifold includes the pad using the pad channels to transfer to the fluid sample to the one or more microfluidic channels in fluid communication with the intake manifold.

In some embodiments, transferring the fluid sample from the pad to the intake manifold includes transferring the fluid sample from the pad to the intake manifold by gravity flow or capillary action.

In some embodiments, detecting one or more analytes in the fluid sample includes using the one or more reagents to detect one or more analytes.

In some embodiments, the one or more analytes include urine, stool, bacteria, glucose, or proteins.

In some embodiments, the one or more reagents emit a visible color or undergo a visible color change when detecting the one or more analytes in the fluid sample.

In some embodiments, the one or more reagents emit a visible color or undergo a visible color change when detecting the one or more analytes over a threshold.

In some embodiments, the one or more reagents emit a visible color or undergo a visible color change in proportion to the concentration of the one or more analytes within the fluid sample.

In some embodiments, analyzing the detected one or more analytes includes the analyzer detecting the visible color or visible color changes.

In some embodiments, the analyzer detects the visible color or visible color changes within the intake manifold or removable wafer.

In some embodiments, the analyzer includes a camera configured to capture one or more images of the intake manifold or removable wafer.

In some embodiments, analyzing the detected one or more analytes includes the console correlating the detected visible color or detected visible color change with a result value and time of day value.

In some embodiments, the result value is above or below a threshold.

In some embodiments, transmitting the results to the computing device includes the analyzer transmitting the results when the analyzer is coupled to a docking station in communication with the computing device.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 8A illustrates a perspective view of the intake manifold including a removable wafer, in accordance with some embodiments.

FIGS. 8B-8C illustrates a perspective view of some components of the removable wafer including a wafer cover, in accordance with some embodiments.

DESCRIPTION

Figure 1:
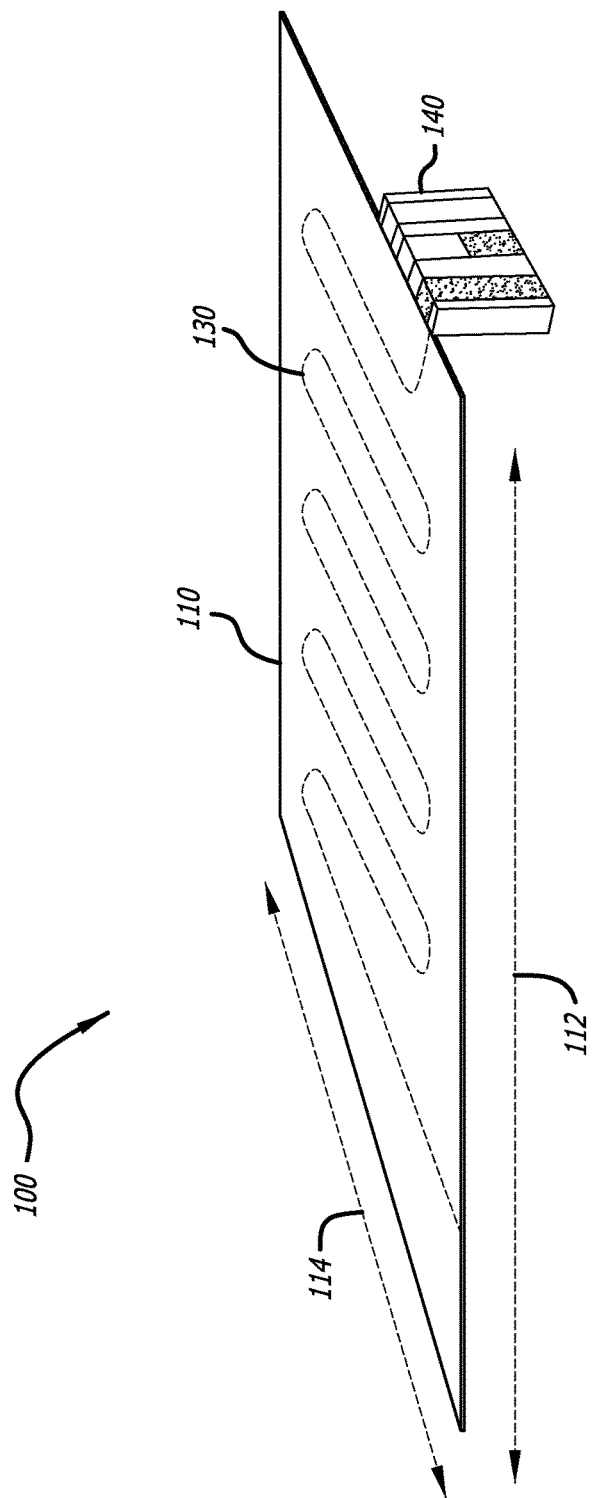
FIG. 1 illustrates a perspective view of a pad of a waste detection system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a pad disclosed herein includes a portion of the pad intended to be near a patient when the pad is used on a patient. Likewise, a "proximal length" of, for example, the pad includes a length of the pad intended to be near the patient when the pad is used on the patient. A "proximal end" of, for example, the pad includes an end of the pad intended to be near the patient when the pad is used on the patient. The proximal portion, the proximal-end portion, or the proximal length of the pad can include the proximal end of the pad; however, the proximal portion, the proximal-end portion, or the proximal length of the pad need not include the proximal end of the pad. That is, unless context suggests otherwise, the proximal portion, the proximal-end portion, or the proximal length of the pad is not a terminal portion or terminal length of the pad.

With respect to "distal," a "distal portion" or a "distal-end portion" of, for example, a pad disclosed herein includes a portion of the pad intended to be near or in a patient when the pad is used on the patient. Likewise, a "distal length" of, for example, the pad includes a length of the pad intended to be near or in the patient when the pad is used on the patient. A "distal end" of, for example, the pad includes an end of the pad intended to be near or in the patient when the pad is used on the patient. The distal portion, the distal-end portion, or the distal length of the pad can include the distal end of the pad; however, the distal portion, the distal-end portion, or the distal length of the pad need not include the distal end of the pad. That is, unless context suggests otherwise, the distal portion, the distal-end portion, or the distal length of the pad is not a terminal portion or terminal length of the pad.

Unless defined otherwise, all technical and scientific terms used herein have the same meaning as commonly understood by those of ordinary skill in the art.

FIG. 1 illustrates a perspective view of a pad 110 of a waste detection system 100, in accordance with some embodiments. In some embodiments, the waste detection system 100 includes the pad 110 coupled to an intake manifold 140. In some embodiments, the pad 110 may be configured to absorb fluid excreted from a patient and transfer the absorbed fluid to the intake manifold 140, which may be configured to test the fluid and detect the presence of one or more of: stool, urine, *Clostridioides difficile* ("*C. Diff*") or the like that will be described in more detail herein.

In some embodiments, the pad 110 includes a pad length 112 and a pad width 114, wherein the pad length 112 may be greater than or equal to the pad width 114. The pad 110 may be configured to include one or more channels 130 within the pad 110 configured to transport the excreted fluid waste from the patient to the intake manifold 140. In some embodiments, the one or more channels 130 may include microfluidic channels in fluid communication with the intake manifold 140. In some embodiments, the pad 110 may have a shape including a square, a rectangle, a polygon or the like. In some embodiments, the channels 130 may be in arranged in various configurations within the pad 110. The arrangement of the various configurations of the channels 130 may be used to maximize the collection area of the channels 130 that collect and transport the absorbed fluids to the intake manifold 140, as will be described in more detail herein. In some embodiments, the channels 130 may be configured to draw fluid from the pad and transfer the fluid to the intake manifold 140 through capillary action, gravity flow, negative pressure flow, self-propulsion or the like. In some embodiments, the channels 130 may be configured to draw fluid from the pad and transfer the fluid to the intake manifold 140 through powered or manually pumped means (e.g., mechanically generated vacuum, electronically generated vacuum, or the like).

Figure 2:
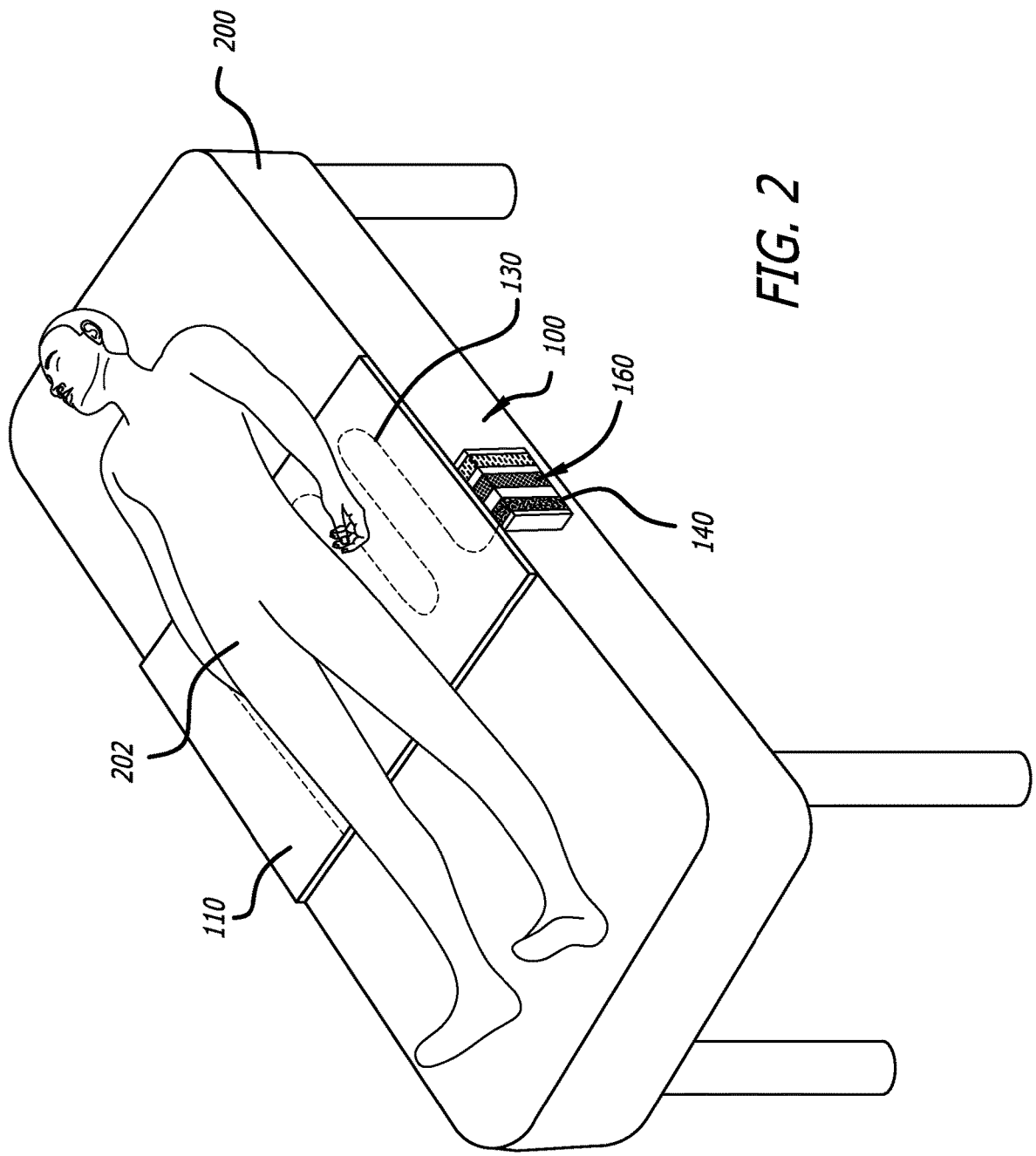
FIG. 2 illustrates a perspective view of the waste detection system, in accordance with some embodiments.

FIG. 2 illustrates a perspective view of the waste detection system 100, in accordance with some embodiments. In some embodiments, the waste detection system 100 may be utilized in a hospital setting, wherein the pad 110 is placed on, or detachably coupled to a medical bed 200 and the intake manifold 140 may also be coupled to the medical bed 200. In some embodiments, the intake manifold 140 may be configured to be coupled to the medical bed 200, wherein the intake manifold 140 is visible to a caretaker (e.g., suspended from the medical bed 200, coupled to an arm rest of the medical bed 200 or the like). In some embodiments, the pad 110 may be placed on the medical bed 200, approximately where the lower abdominal region (e.g., groin region) is configured to rest wherein a patient 202 is in a supine position, a prone position, a right lateral recumbent, a left lateral recumbent, a Fowler's position or the like. Although the waste detection system 100 may be used in a hospital setting, it can be appreciated that the waste detection system 100 may be utilized in a home setting, a wheelchair setting or the like, all of which are considered. In some embodiments, the pad 110 may be detachably coupled to the medical bed 200, detachably coupled to a sheet on the medical bed 200 or the like, and the patient 202 may sit or lay over the pad 110, as illustrated in FIG. 2. The patient 202 is free to move around the pad 110. If the patient 202 has a bowel movement and excretes a fluid (e.g., urine, stool, blood or a combination thereof), a portion of the fluid may be acquired or retained by the pad 110 through wicking the fluid away from the patient 202 and absorbing the fluid into the pad 110. The portion of the fluid retained by the pad 110 will be referred to as a fluid sample. The fluid sample may be configured to be directed by the pad 110 into the one or more channels 130, where the fluid sample is further drawn into the intake manifold 140. In some embodiments, the intake manifold 140 is configured to receive therein the fluid sample from the one or more channels 130. In some embodiments, the intake manifold 140 may be configured to include one or more reagents 160 that may be configured to detect the presence of urine or stool in the fluid sample within the intake manifold 140 that will be described in more detail herein. If the intake manifold 140 detects the presence of urine or stool within the fluid sample, the one or more reagents 160 or the intake manifold 140 itself, or a portion of the intake manifold 140 may be configured to undergo a visual change including a visual color change that will be described in more detail herein, configured to alert a caretaker that a bowel movement has occurred. In some embodiments, the waste detection system 100 or a portion thereof (e.g., the intake manifold 140, the pad 110) may be configured to be disposable.

Figure 3A:
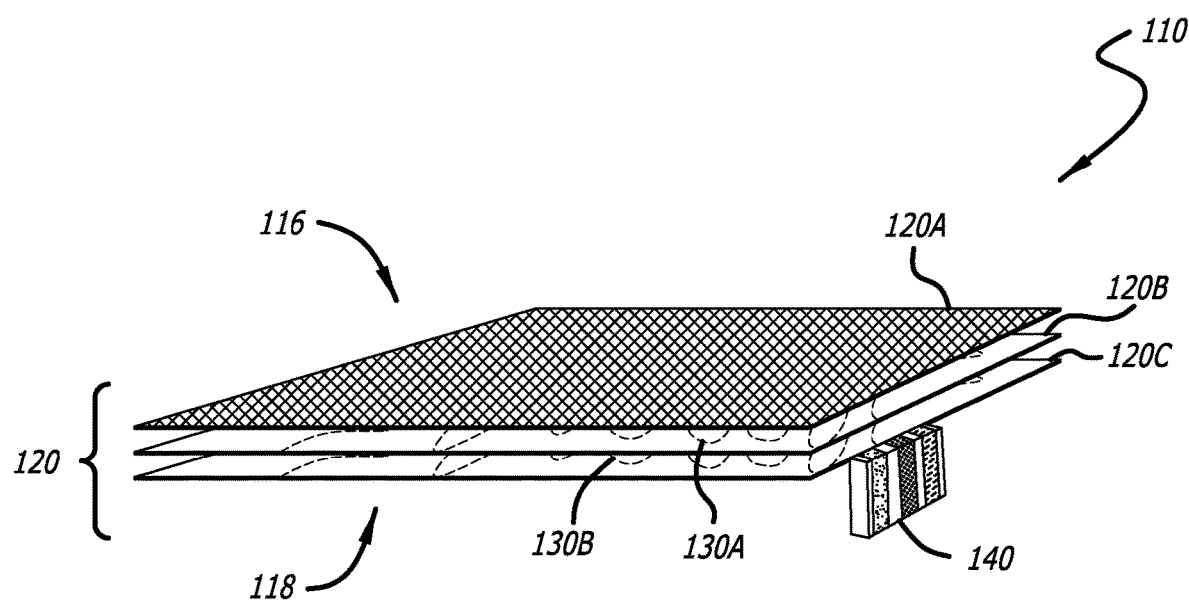
FIG. 3A illustrates an exploded perspective view of the pad, in accordance with some embodiments.

FIG. 3A illustrates an exploded perspective view of the pad 110, in accordance with some embodiments. In some embodiments, the pad 110 may include a proximal side 116 and a distal side 118, wherein the proximal side 116 is closest to the patient 202 or in physical contact with the patient 202 and the distal side 118 is furthest away from the patient 202. In some embodiments, the pad 110 may be configured to be constructed of or include one or more layers 120. In some embodiments, a portion of each of the one or more layers 120, or the entirety of each layer of the one or more multiple layers 120 may be configured to have absorbent properties, wicking properties or a combination thereof, that will be described in more detail herein. In some embodiments, one or more of the layers 120 may be configured to include the one or more channels 130 that may be organized into various configurations. The various configurations may be engineered to receive a fluid sample from any point on the pad 110 The one or more channels 130 may be secured to a surface of each layer 120 or integrated within each layer 120. The channels 130 may be secured to the surface by an adhesive, clips, snaps, or the like. The microfluidic channels may be integrated within each layer 120. Other mechanisms of securing the one or more microfluidic channel 130 to the layer 120 are also considered.

In some embodiments, each layer of the multiple layers 120 may be configured to have different properties, constructed of different materials or a combination thereof. For example, as illustrated in FIG. 3A, the pad 110 includes three layers, a first proximal layer 120A, a second middle layer 120B having a first microfluidic channel 130A and a third distal layer 120C having a second microfluidic channel 130B. The entirety of the first proximal layer 120A may be configured to having wicking properties configured to wick a fluid sample away from a skin surface of a patient and direct the fluid sample to be absorbed by the second middle layer 120B and the third distal layer 120C, wherein the entirety of the second middle layer 120B and the entirety of the third distal layer 120C have absorbent properties. The second middle layer 120B may be configured to direct the fluid sample to the first microfluidic channel 130A and the third distal layer 120C may be configured to direct the fluid sample to the second microfluidic channel 130B. In some embodiments, the pad 110 having more than one microfluidic channel 130 allows for fluid flow of the fluid sample to continue if one of the channels 130 is blocked by fecal debris or other solid matter. In some embodiments, each layer of the multiple layers 120 may be constructed of or include: polyester, polyurethane, polypropylene, nylon, bamboo fiber, wool fiber, cotton fiber, hemp fiber, sodium polyacrylate or a combination thereof. In some embodiments, each layer 120 may be configured to be textured or have patterned ridges. In some embodiments, the distal side 118 of the pad 110 may include fluid proof properties. For example, as illustrated in FIG. 3A, the distal side 118 of the third distal layer 120C may include vinyl, polyvinyl, a laminate, a synthetic plastic or the like, configured to maintain the fluid sample within the pad 110 and prevent the fluid sample from leaking through the pad 110 to the medical bed 200 or the like. It can be appreciated that greater or lesser number of layers are also contemplated. In some embodiments, the pad 110 may be disposable. The distal side 118 of the pad 110 may be configured to include one or more attachments configured to secure the pad 110 to the medical bed 200, a sheet on the medical bed 200 or the like. In some embodiments, the one or more attachments may include hook and loop fasteners, adhesive tape, magnetic fasteners, butterfly clips or the like.

Figure 3B:
FIG. 3B illustrates a cross sectional view of the microfluidic channel within the microfluidic cavity of the pad, in accordance with some embodiments.

FIG. 3B illustrates a cross sectional view of the microfluidic channel 130 within the pad 110, in accordance with some embodiments. In some embodiments, the pad 110 includes a microfluidic cavity 138 configured to contain the microfluidic channel 130 therein. In some embodiments, a portion of the one or more layers 120 may be configured to have wicking properties and a portion of the one or more layers 120 may be configured to have absorbent properties. In some embodiments, the microfluidic cavity 138 may be located in a wicking portion 122, an absorbent portion 124, or a combination thereof. In some embodiments, the microfluidic channel 130 may include microfluidic tubing having a lumen 132 therein, the lumen 132 being in fluid communication with the intake manifold 140. The microfluidic tubing may be configured to include one or more intake holes 134 in fluid communication with the lumen 132. In some embodiments, the wicking portion 122 draws the fluid sample away from the patient 202, through the wicking portion 122 into the absorbent portion 124. The fluid sample may be drawn from the absorbent portion, through the one or more intake holes 134 into the lumen 132 and further on to the intake manifold 140. In some embodiments, the wicking portion 122 may include wicking channels, straw shaped channels configured to direct fluid from the skin surface of the patient to the absorbent portion 124.

Figure 4B:
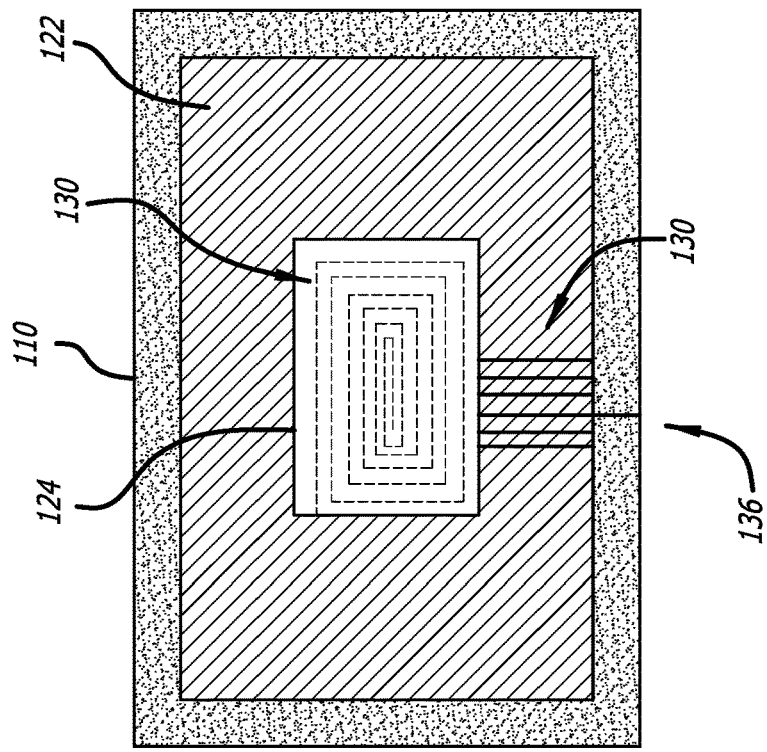
FIGS. 4A-4B illustrates plan views of different embodiments of the pad, in accordance with some embodiments.
Figure 4A:
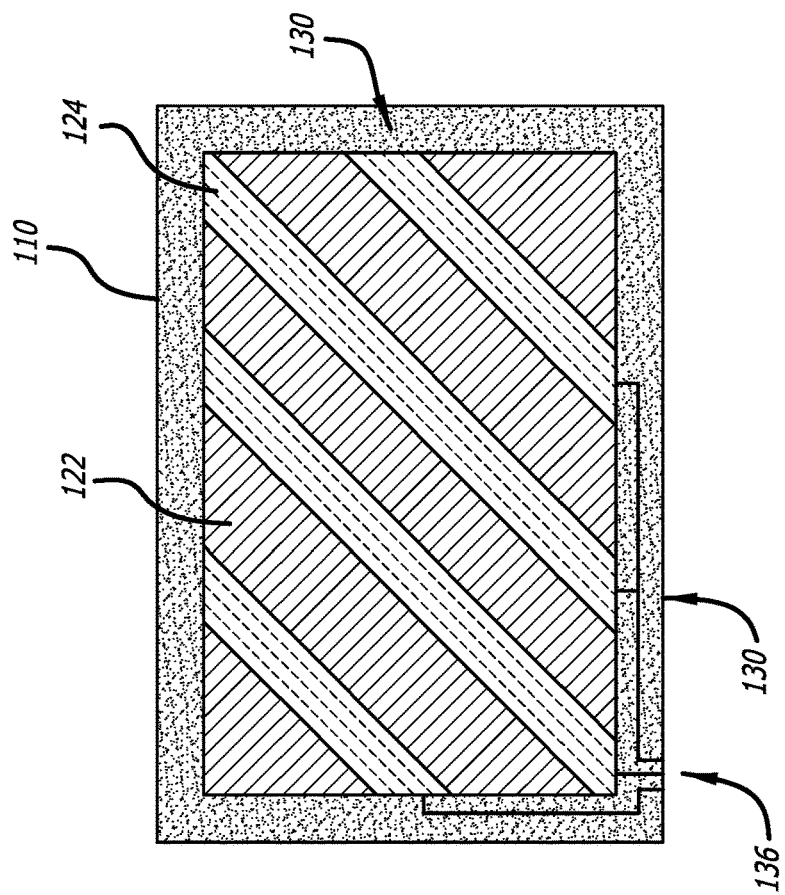

FIGS. 4A-B illustrates plan views of different embodiments of the pad 110, in accordance with some embodiments. As illustrated in FIG. 4A, the absorbent portions 124 may be configured in diagonal bands, having two or more channels 130 within each diagonal band. In some embodiments, the channels 130 may funnel to a microfluidic port 136 configured to couple with the intake manifold 140 and maintain the fluid communication between the channels 130 and the intake manifold 140. In some embodiments, the microfluidic port 136 may combine the fluid samples from multiple channels 130 into one fluid sample or may keep the fluid sample from each microfluidic channel 130 separate. In an embodiment, as illustrated in FIG. 4B, the wicking portion 122 may be larger than the absorbent portion 124. In this embodiment, the absorbent portion 124 includes the microfluidic channel 130 funneling the fluid sample to the microfluidic port 136. In some embodiments, the wicking portion 122 may be equal to or less than the absorbent portion 124.

Figure 5A:
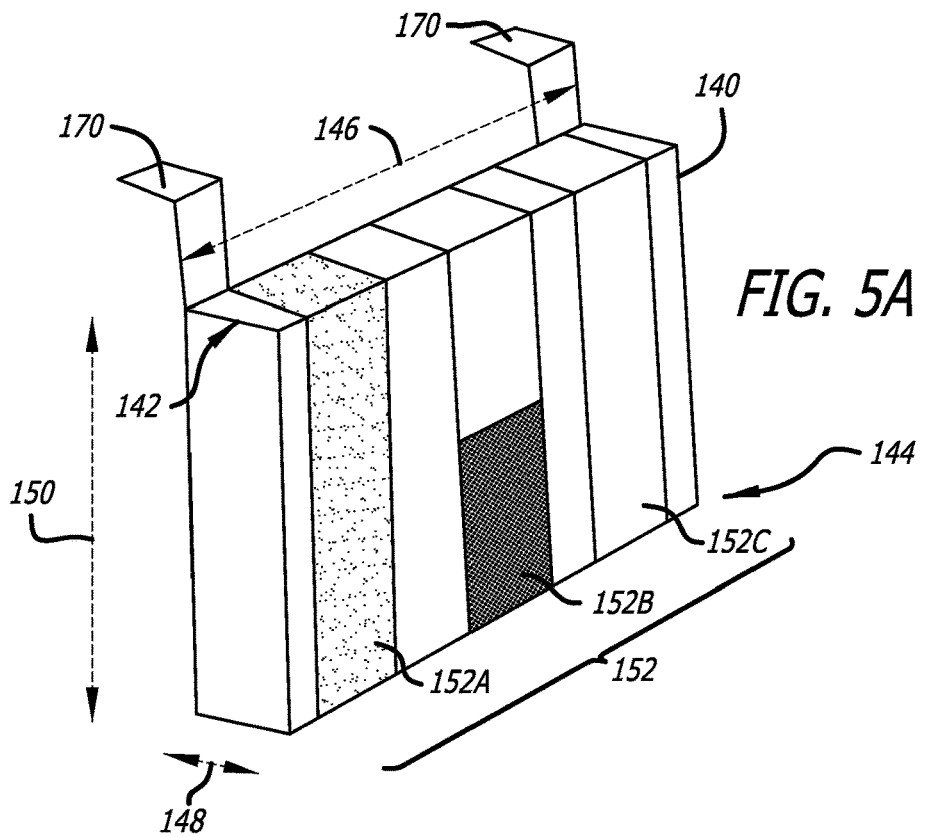
FIG. 5A illustrates a perspective view of the intake manifold, in accordance with some embodiments.

FIG. 5A illustrates a perspective view of the intake manifold, in accordance with some embodiments. In some embodiments, the intake manifold 140 has a proximal side 142, a distal side 144, a length 146, a width 148 and a height 150. The intake manifold 140 may be in the shape of a rectangular prism, a triangular prism or the like. In some embodiments, the intake manifold 140 may be constructed of a clear plastic polymer (e.g., acrylic, polycarbonate, polyethylene terephthalate, amorphous copolyester, polyvinyl chloride, or the like). In some embodiments, the channels 130 may be configured to couple to and be in fluid communication with the intake manifold 140 at the proximal side 116 or the distal side 118 of the intake manifold 140 and may be configured to be detachably coupled from the intake manifold 140. In some embodiments, the intake manifold 140 may be disposable or reusable and may be configured to be sterilized in between uses.

Figure 5B:
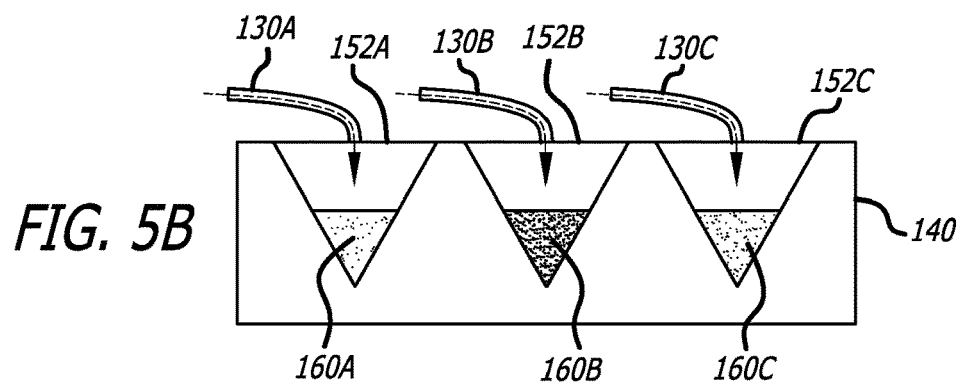
FIG. 5B illustrates a cross sectional view of the intake manifold including the one or more chambers, in accordance with some embodiments.

The intake manifold 140 may be configured to receive therein one or more volumes of the fluid sample. In some embodiments, the intake manifold 140 may include one or more chambers 152. In some embodiments, each chamber of the one or more chambers 152 may be coupled to and in fluid communication with a different microfluidic channel 130 of the pad 110 and the entire fluid sample may be delivered to the chamber 152 by the microfluidic channel 130. For example, as illustrated in FIG. 5B, wherein the pad 110 includes three channels 130, the intake manifold 140 may include three chambers 152, wherein the first chamber 152A is configured to receive the fluid sample from the first microfluidic channel 130A, the second chamber 152B is configured to receive the fluid sample from the second microfluidic channel 130B, and the third chamber 152C is configured to receive the fluid sample from the third microfluidic channel 130C. In some embodiments, wherein the pad 110 includes the microfluidic port 136, each chamber 152 may be configured to receive the fluid sample combined from the multiple layers 120 and the multiple channels 130. In some embodiments, each microfluidic channel 130 may be configured to be coupled to the intake manifold 140 and within the intake manifold 140, the fluid sample may be evenly divided between the one or more chambers 152. In some embodiments, the one or more chambers 152 may extend through a portion of the intake manifold 140 or the entire height 150 of the intake manifold 140.

In some embodiments, as illustrated in FIG. 5A, the intake manifold 140 may include one or more hooks 170 configured to suspend the intake manifold 140 from the medical bed 200. In some embodiments, the intake manifold 140 may include one or more magnets, hook and loop fasteners or the like to detachably couple the intake manifold 140 to the medical bed 200. Other mechanisms of detachably coupling the intake manifold 140 to the medical bed 200 are also considered.

FIG. 5B illustrates a cross sectional view of the intake manifold 140 including the one or more chambers 152, in accordance with some embodiments. In some embodiments, the intake manifold 140 may be configured to slidably receive the one or more channels 130. In some embodiments, the microfluidic channels may be coupled to the intake manifold 140 by a magnetic fit, an interference fit, a press fit, snap fit, a twist fit or the like. In some embodiments, the one or more chambers 152 may be the shape of a cylinder, a rectangular prism, a triangle prism, an inverted cone or the like. In some embodiments, as illustrated in FIG. 5B, each chamber 152 may be configured to include the one or more reagents 160 configured to detect the presence of urine or stool in the fluid sample excreted from the patient. In some embodiments, the one or more reagents 160 may include chemicals configured to detect changes in pH including but not limited to methyl red or bromothymol blue, the presence of proteins such as albumin, the presence of blood including but not limited to peroxide and tetramethylbenzidine, the presence of C. Diff. including but not limited to glutamate dehydrogenase and the like. In some embodiments, the one or more reagents 160 may reside in a solution form, a liquid form or a powdered form within the chamber 152. In some embodiments, the one or more reagents 160 may be configured to emit a visible color or visible color change in the fluid sample in the presence of urine, stool, blood, *C. Diff.* or a combination thereof. In some embodiments, the visible color or color change within the fluid sample may be used to alert a caretaker that bowel movement has occurred through presence of waste in the fluid sample. In some embodiments, the visible color or color change within the fluid sample may have different meanings. For example, a color change of yellow to blue may indicate the presence of urine while a color change of blue to red may indicate the presence of *C. Diff.* Both visible color changes indicate to the caretaker that a bowel movement has occurred, however the presence of *C. Diff.* indicates different cleaning precautions must be undertaken versus just the presence of urine or stool. Advantageously, the visible color or visible color change within the fluid sample in the intake manifold 140 may be used to timely alert a caretaker that a bowel movement has occurred without the need to question or visually inspect the patient. The visible color or visible color change may indicate to the caretaker that immediate attention and/or cleaning and disposal of the waste detection system 100 is required.

In some embodiments, the fluid sample may enter the chamber 152 through gravity flow, capillary action, low pressure flow, or the like. The fluid sample may enter into the chamber 152 and mix with the one or more reagents 160, wherein the one or more reagents 160 react with the fluid sample in a chemical reaction or a biochemical assay to detect the presence of urine or stool within the fluid sample. In some embodiments, each chamber 152 may be configured to include the same one or more reagents, or different reagents. For example, the first chamber 152A may be configured to include the one or more reagents 160 configured to test for the presence of urine within the fluid sample. The second chamber 152B may be configured to include the one or more reagents 160 configured to test for the presence of stool within the fluid sample. The third chamber 152C may be configured to include the one or more reagents 160 configured to test for the presence of *C. Diff.* within the fluid sample. It can be appreciated that the one or more reagents 160 may include reagents to test additional parameters of the fluid sample including presence of blood cells (red blood cells, white blood cells), presence of nitrites or ions such as sodium, potassium, calcium, phosphate, or proteins, all of which are considered.

Figure 5C:
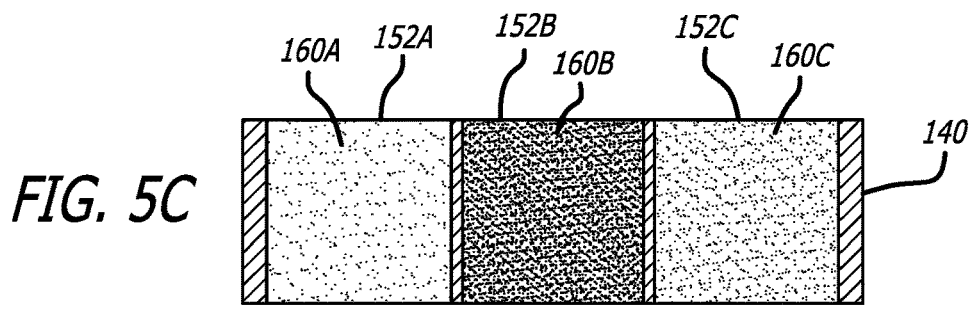
FIG. 5C illustrates a plan view of a method of detecting waste excreted from the patient, in accordance with some embodiments.

FIG. 5C illustrates a plan view of a method of detecting waste excreted from the patient 202, in accordance with some embodiments. In some embodiments, as illustrated in FIG. 5C, the intake manifold 140 may include the first chamber 152A including the one or more reagents 160 configured to test for urine, the second chamber 152B including the one or more reagents 160 configured to test for stool and the third chamber 152C including the one or more reagents 160 configured to test for *C. Diff.* The first chamber 152A and the third chamber 152C do not emit a visible color or demonstrate changed in color, indicating the absence of urine or *C. Diff.* within the fluid sample. The second chamber 152B does emit a visible color change indicating the presence of stool within the fluid sample.

Figure 6:
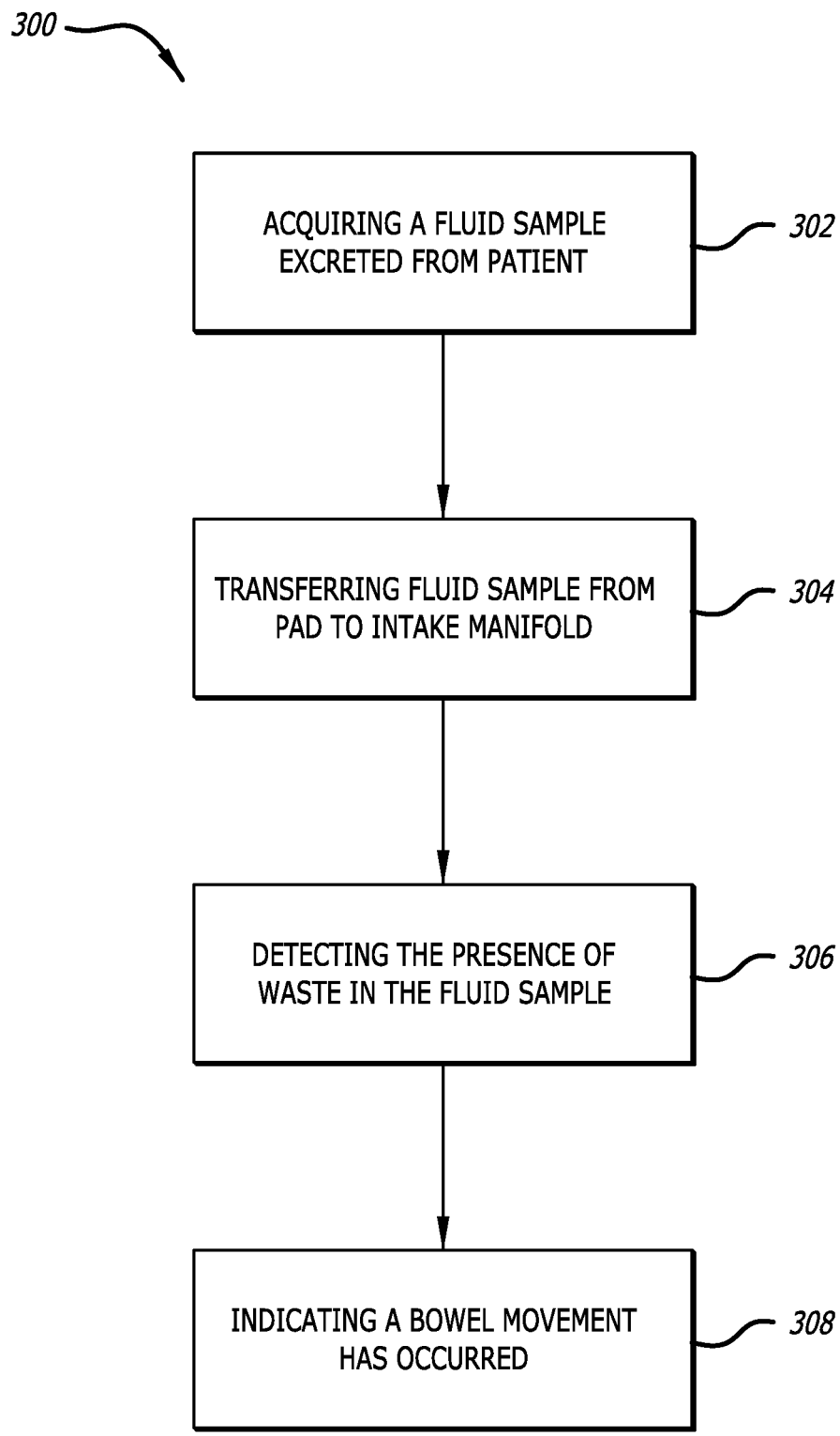
FIG. 6 illustrates a flow chart of an exemplary method of detecting the presence of waste in a fluid sample excreted from a patient using the waste detection system, in accordance with some embodiments.

FIG. 6 illustrates a flow chart of an exemplary method 300 of detecting the presence of waste in a fluid sample excreted from a patient using the waste detection system 100, in accordance with some embodiments. In some embodiments, the method 300 includes acquiring a fluid sample excreted from a patient on a pad 110 (block 302). In some embodiments, acquiring including absorbing the fluid sample using the pad 110 of the waste detection system 100. In some embodiments, acquiring the fluid sample excreted from the patient on the pad 110 includes the pad 110 being placed under a lower abdominal region of the patient. In some embodiments, acquiring the fluid sample includes the wicking portion 122 wicking away the fluid sample and the absorbent portion 124 absorbing the fluid sample. In some embodiments, the pad 110 includes one or more layers 120 configured to wick away an excreted fluid sample from the skin surface of the patient and absorb the fluid sample into one or more channels 130 on or within the one or more layers 120 of the pad 110.

The method 300 further includes transferring the fluid sample from the pad 110 to an intake manifold 140 (block 304). In some embodiments, the intake manifold 140 may be configured to have the one or more chambers 152 configured to receive therein the fluid sample and have therein one or more reagents 160 configured to detect the presence of urine or stool within the fluid sample. In some embodiments, the intake manifold 140 may be fluidly connected to the one or more channels 130. In some embodiments, transferring the fluid sample to the intake manifold 140 occurs through capillary action, negative pressure flow, gravity flow or the like. The method 300 further includes detecting the presence of waste in the fluid sample (block 306). In some embodiments, detecting includes using the one or more reagents 160 in a chemical reaction or biochemical assay within the one or more chambers 152. In some embodiments, waste includes urine, stool, blood, or *Clostridioides difficile*. The method 300 further includes indicating a bowel movement has occurred (block 308). In some embodiments, indicating includes the one or more reagents 160 emitted a visible color or changing visible colors within the intake manifold 140 due to the presence of urine or stool within the fluid sample.

Figure 7A:
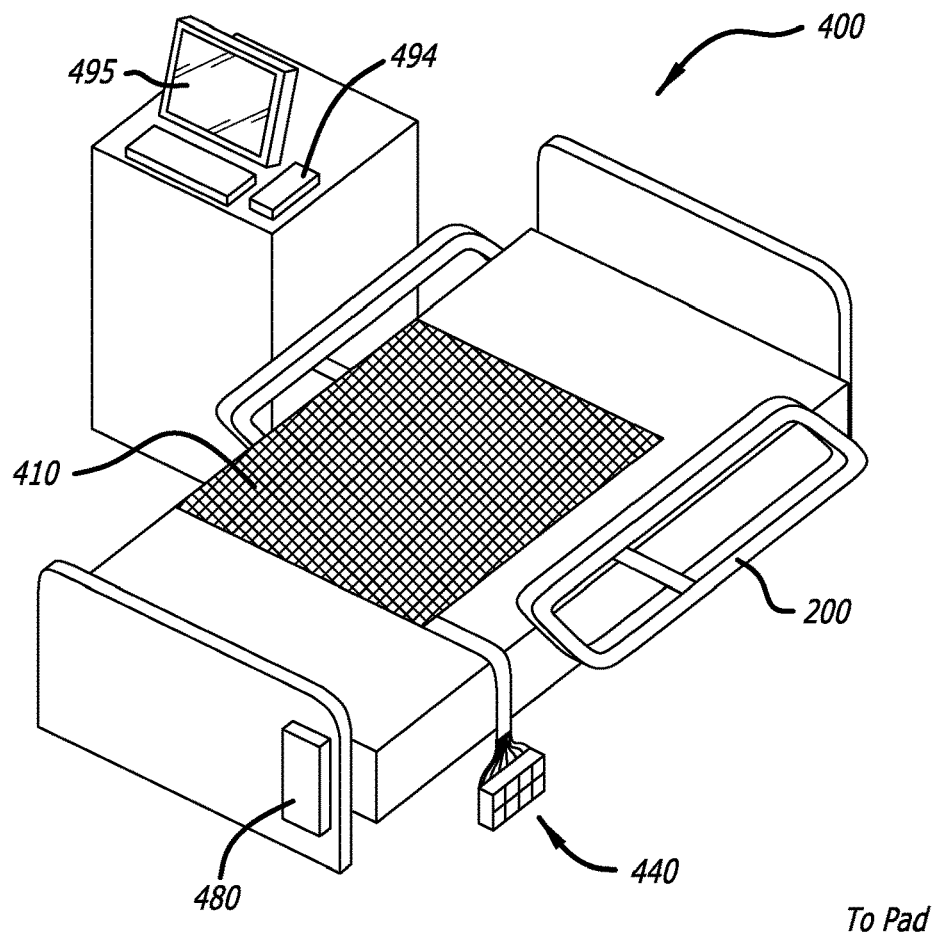
FIG. 7A illustrates a perspective view of the waste detection system in a hospital setting, in accordance with some embodiments.
Figure 7B:
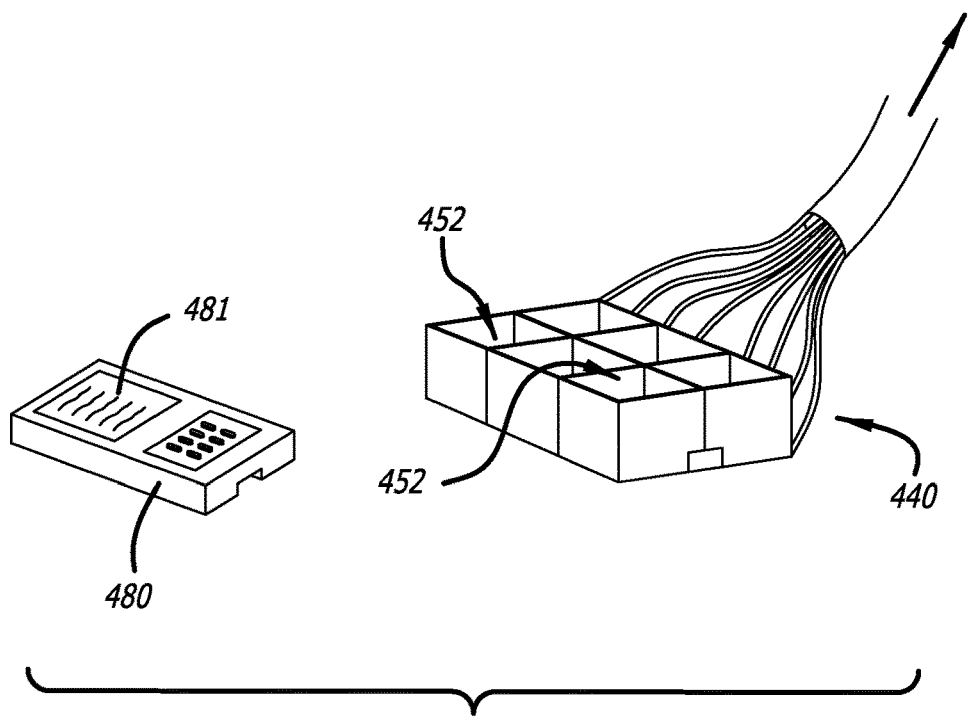
FIG. 7B illustrates a perspective view of some components of the waste detection system including an intake manifold and an analyzer, in accordance with some embodiments

FIGS. 7A-7B illustrates a perspective view of some components of a waste detection system 400, in accordance with some embodiments. In some embodiments, the pad 410, in fluid communication with the intake manifold 440, may be coupled to the hospital bed 200. In some embodiments, the waste detection system 400 further includes an analyzer 480. The analyzer 480 may be configured to detect a visible color or visible color change in the intake manifold 440, as will be described in more detail herein. In some embodiments, the analyzer 480 may be coupled to the hospital bed 200. In some embodiments, the intake manifold 440 may be detachable from the pad 410. Having the intake manifold 440 being detachable from the pad 410 allows for the ability to generate an intake manifold 440 with specific reagents therein. Furthermore, having the intake manifold 440 being detachable allows the intake manifold 440 to be reusable. In some embodiments, the analyzer 480 may be detachably coupled to a docking station 494. In some embodiments, the docking station 494 may be in communication with a computing device 495. In some embodiments, when the analyzer 480 is coupled to the docking station 494, the analyzer 480 may be configured to transmit the detected data to either of the docking station 494 or the computing device 495. In some embodiments, the docking station 494 may be within a patient's room or may be in a central location. In some embodiments, the docking station 494 may be wired to the computing device 495 or in wireless communication with the computing device 495.

As illustrated in FIG. 7B, the intake manifold 440 may be detachable from the pad 410. The intake manifold 440 may include one or more chambers 452, as will be described in more detail herein. In some embodiments, a portion of the intake manifold 440 may be configured to be removable. In some embodiments, the portion of the intake manifold 440 that is removable may be configured to be inserted into the analyzer 480 as will be described in more detail herein. The portion of the intake manifold 440 that is removable may include a cover that will be described in more detail herein.

FIG. 8A illustrates a perspective view the intake manifold 440 including a removable wafer 454, in accordance with some embodiments. In some embodiments, the intake manifold 440 may include one or more chambers 452A-452F wherein each chamber in the one or more chambers 452A-452F is configured to receive therein a portion of the fluid sample. FIG. 8A illustrates 6 chambers 452A-452F, although greater or lesser numbers of chambers are also contemplated. In some embodiments, each chamber 452 may be configured to includes a separate reagent 460 or a combination of reagents (as indicated in FIG. 8A by the different patterns in each chamber 452A-452F) that are configured to detect the one or more analytes within the fluid sample. The reagent 460 or combination of reagents 460 may be configured to indicate detection of the one or more analytes within the fluid sample by the generation of a visible color or a visible color change. In some embodiments, the one or more analytes may include urine, stool *C. Diff*, glucose, proteins, bacteria, or the like. In some embodiments, the reaction of the one or more reagents 460 with one or more analytes within the fluid sample may be referred to hereon as an assay. Each chamber 452 may include a different assay or may include redundant assays configured to allow the clinician to confirm the results of the assays. In some embodiments, the intake manifold 440 may include a standardized panel of assays for detecting the presence of urine or stool in the fluid sample, an advanced panel of assays for detecting the presence of bacteria, *C. Diff*, or glucose in addition to urine or stool in the fluid sample, a disease state specific panel of assays, a treatment plan panel of assays, or a combination thereof. In some embodiments, the reagent 460 or combination of reagents 460 may be configured to generate a visible color or a visible color change when the concentration of the analyte reach a threshold within the fluid sample. In some embodiments, the reagent 460 or combination of reagents 460 may be configured to generate a visible color or a visible color change in proportion to the concentration of the analyte (e.g., a color gradient).

In some embodiments, the intake manifold 440 may be constructed of a clear hardened plastic (e.g., acrylic, polycarbonate, polyethylene terephthalate, amorphous copolyester, polyvinyl chloride, or the like). The intake manifold 440 may be 3D printed, injection molded or the like. The intake manifold 440 may be formed contiguously or may be formed from a plurality of pieces. In some embodiments, the intake manifold 440 may include an intake manifold lid 441 configured to secure the fluid sample within each chamber 454. In some embodiments, the intake manifold lid 441 may be configured to form a fluid tight seal with the intake manifold 440. In some embodiments, the intake manifold lid 441 may be clear. In some embodiments, the intake manifold 440 may include a removable wafer 454, wherein the removable wafer 454 may be configured to receive therein a defined volume of fluid including a portion of the fluid sample and one or more reagents 460 from each chamber 452 within the intake manifold 440. The removable wafer 454 may be removed from the intake manifold 440, sealed and inserted into the analyzer 480 to determine and confirm the presence of one or more analytes within the fluid sample.

FIGS. 8B-8C illustrates a perspective view of some components of the removable wafer 454 including a wafer cover, in accordance with some embodiments. In some embodiments, the removable wafer 454 may be configured to be slidably removed from the intake manifold 440. In some embodiments, the removable wafer 454 may be in the shape of a cylindrical disk, rectangular prism, or the like. The removable wafer 454 may be configured to include two or more wafer compartments 455 configured to hold therein a defined volume of a portion of the fluid sample and the one or more reagents 460. In some embodiments, the number of wafer compartments 455A-455F may equal the number of chambers 452A-452F in the intake manifold 440, wherein each of the wafer compartments 455 corresponds to the respective chamber 452 in the intake manifold 440. The wafer compartments 455 may be in fluid communication with the chambers 452 in the intake manifold 440. The removable wafer 454 may be configured to be sealable (e.g., sealed with a fluid tight seal), allowing the removable wafer 454 to be inserted into the analyzer 480 for analysis. In an embodiment, the removable wafer 454 may include a wafer cover 456 configured to create a fluid tight seal with the removable wafer 454. In this embodiment, the wafer cover 456 may be coupled to the removable wafer 454 through a press fit, a snap fit, an interference fit or the like, as illustrated in FIG. 8B. In this embodiment, the wafer cover 456 may be configured to be coupled to the removable wafer 454 after the removable wafer 454 is removed from the intake manifold 440. The wafer cover 456 may also be clear, configured to allow the analyzer 480 to analyze the results of the assays, as illustrated in FIG. 8C. In this embodiment, each of the removable wafer 454, or the wafer cover 456 may be disposable. Advantageously, the removable wafer 454 allows the intake manifold 440 to remain coupled to the pad 410 and only the removable wafer 454 is moved to the analyzer 480 for analysis.

Figure 9A:
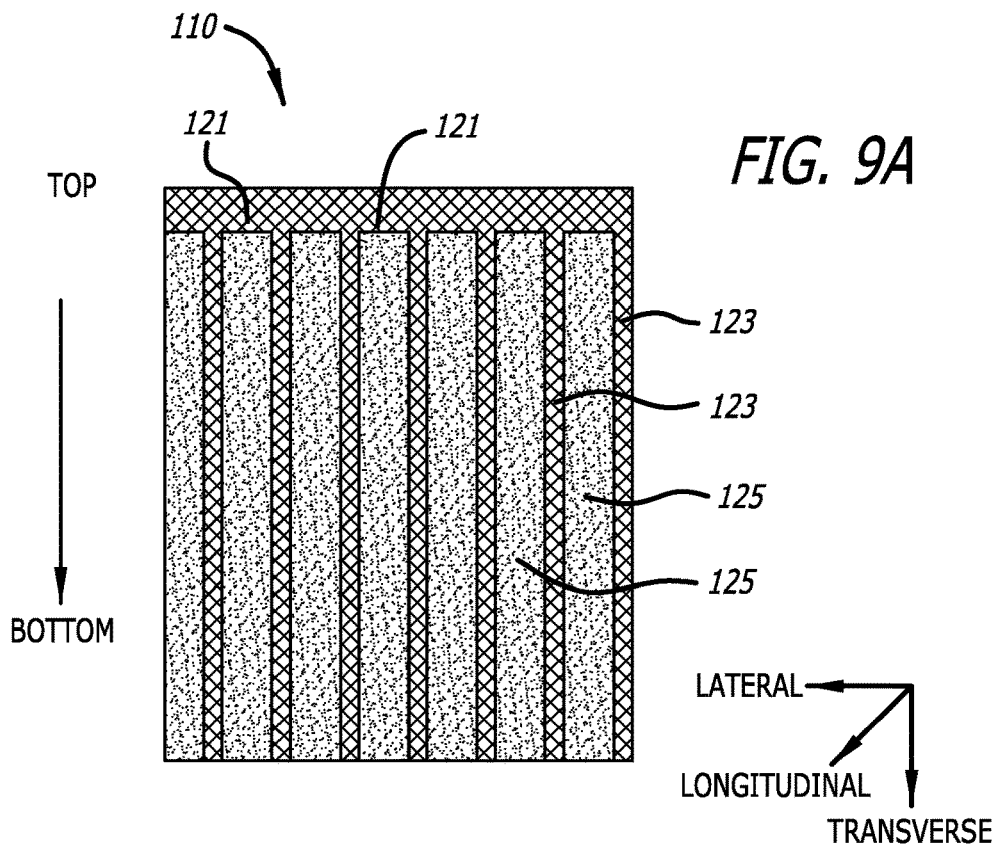
FIGS. 9A-9B illustrate cross sectional views of the pad, in accordance with some embodiments.
Figure 9B:
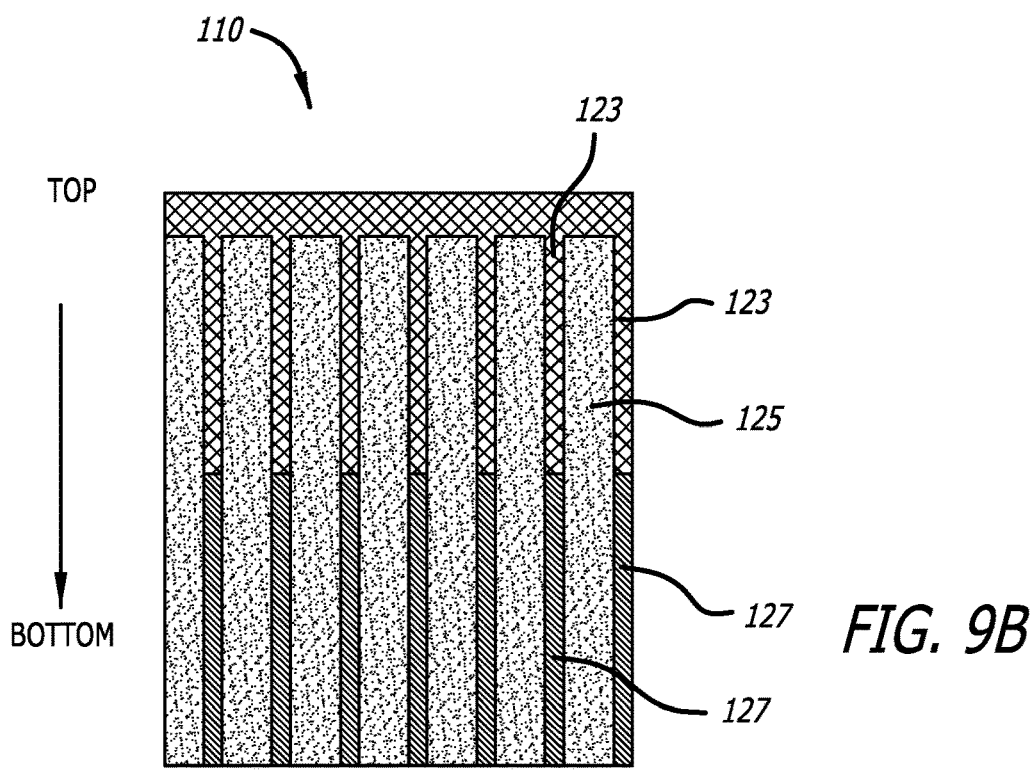

FIGS. 9A-9B illustrate cross sectional views of the pad 110 of FIG. 3A, in accordance with some embodiments. In some embodiments, the pad 110 may have pad channels 121 that are in fluid communication with the microfluidic channels 130. In some embodiments, the pad channels 121 may be oriented in the transverse direction, directing fluid flow from a top layer towards the bottom. In some embodiments, the pad channels 121 may direction fluid into the microfluidic channels 130. In some embodiments, the pad channels 121 may be defined by wicking fiber 123 with absorbent material 125 therebetween. The wicking fiber 123 draws fluid through the wicking fiber 123 to the absorbent material 125, allowing the fluid multiple pathways to travel to reach the microfluidic channels 130. In some embodiments, the wicking fiber 123 may include bamboo fiber, cotton fiber, hemp fiber, microfiber, or the like. In some embodiments, the absorbent material 125 may include polyacrylate, other synthetic resins, or absorbent material.

In some embodiments, a portion of, or the entire wicking fiber 123 may be covered with a hydrophilic coating 127 as illustrated in FIG. 9B. In some embodiments, the hydrophilic coating 127 may be configured to create a hydrophilic gradient in the direction of gravity flow. The hydrophilic gradient may be configured to provide a continuous driving force, by capillary action, for liquid to flow from the top layer to the microfluidic channels 130 and to the intake manifold 140. Other structures configured to facilitate fluid transportation through the pad (e.g., cylindrical wicking fiber surrounded by super absorbent material, a super hydrophilic layer included as a bottom layer, or the like) are also considered.

Figure 10:
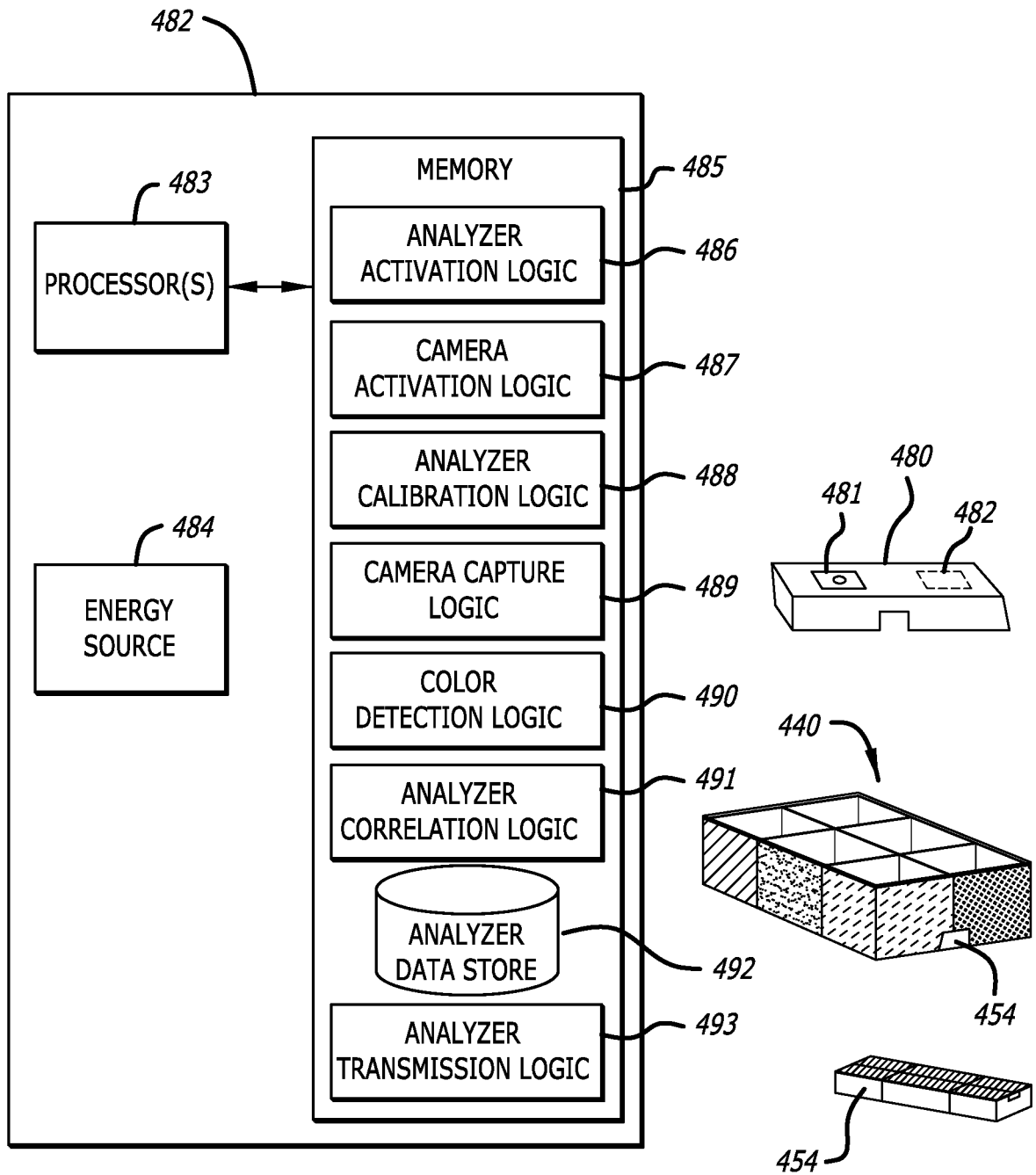
FIG. 10 illustrates a block diagram of some components of the analyzer including a console, in accordance with some embodiments.

FIG. 10 illustrates a block diagram of some components of the waste detection system 400 including a console 482 of the analyzer 480, in accordance with some embodiments. In some embodiments, the analyzer 480 includes the console 482. In some embodiments, the console 482 includes one or more processors 483, an energy source 484, non-transitory computer readable medium ("memory") 485, and a plurality of logic modules. In some embodiments, the energy source 484 may include a rechargeable battery. In some embodiments, the energy source 484 may be configured to be recharged when the analyzer 480 is coupled to the docking station 494. In some embodiments, the plurality of logic modules may include one or more of: an analyzer activation logic 486, a camera activation logic 487, an analyzer calibration logic 488, a camera capture logic 489, a color detection logic 490, an analyzer correlation logic 491, an analyzer transmission logic 492, and an analyzer data store 493. In some embodiments, the analyzer activation logic 486 may be configured to activate the analyzer 480. In some embodiments, the analyzer activation logic 486 may be activated when the intake manifold 440 or the removable wafer 454 is inserted into the analyzer 480.

In some embodiments, the camera activation logic 487 may be configured to activate a camera 481 within the analyzer 480. In some embodiments, the camera 481 may be activated when the intake manifold 440 or the removable wafer 454 is slidably received by the analyzer 480. In some embodiments, the camera 481 may be activated by the user. In some embodiments, the analyzer calibration logic 488 may be configured calibrate the analyzer 480. The analyzer 480 may be configured to calibrate to one or more specific colors or color changes based upon the assays contained within the intake manifold 440 or removable wafer 454. For example, if the intake manifold 440 includes only disease specific assays that include 3 specific colors or color changes, the analyzer calibration logic 488 may be configured to calibrate those 3 specific colors or color changes. In some embodiments, the analyzer 480 may be calibrated on a user defined timetable (e.g., before every use, before a defined number of uses, or at the start of the day). In some embodiments, the camera capture logic 489 may be configured to activate the camera 481 to capture one or more images of a portion of or the entire manifold 440 or a portion of or the entire removable wafer 454. In some embodiments, the color detection logic 490 may be configured to detect the color or color change within the captured image.

In some embodiments, the analyzer correlation logic 491 may be configured to correlate the captured images of the intake manifold 440 with a positive or negative result (e.g., color change in the intake manifold 440). In some embodiments, the analyzer correlation logic 491 may be configured to detect the presence of color or color change within the intake manifold 440, detect and interpret the type of reaction that has occurred within the intake manifold 440 based on the color or colors present, or a combination thereof. In some embodiments, the analyzer correlation logic 491 may be configured to interpret the color or color change within the intake manifold 440 by correlating the detected color or detected color change with a reference color pad. The reference color pad may be saved easily accessed by the console 482 or may be located on the intake manifold 440 or the removable wafer 454. In some embodiments, the analyzer correlation logic 491 may be configured to detect and interpret the type of reaction that has occurred within the intake manifold 440 by correlating the detected color or color gradient with a standardized reference color pad. In some embodiments, the analyzer correlation logic 491 may be configured to interpret a conclusively positive or conclusively negative result. In some embodiments, the analyzer correlation logic 491 may be configured to detect and interpret shades of the color or color change as different results. For example, the shade of color may correlate to the concentration of an analyte within the intake manifold 440. In some embodiments, the analyzer correlation logic 491 may be configured to generate a numerical value corresponding to the detected color. In some embodiments, if the numerical value is over an established threshold, the console 482 will return a positive result value and if the numerical value is below the established threshold, the console 482 will return a negative result value. In some embodiments, the numerical value may correspond to the concentration of an analyte and the console 482 may return a result value, indicating the concentration of the analyte. In some embodiments, the analyzer correlation logic 491 may be configured to correlate a time of day value with the result value and the captured image of the intake manifold 440 or the removable wafer 454.

In some embodiments, the analyzer transmission logic 492 may be configured to transmit the result value, the corresponding time of day value and the captured image to a computing device 495 or electronic medical record system ("EMR"). In some embodiments, the analyzer transmission logic 492 may be configured to transmit the result value, the corresponding time of day value and captured image to the computing device or EMR system when the analyzer 480 is coupled to the docking station 494. In some embodiments, the analyzer data store 493 may be configured to store the numerical value, the result value, the corresponding time of day value, and the corresponding image captured by the camera 481.

Figure 11:
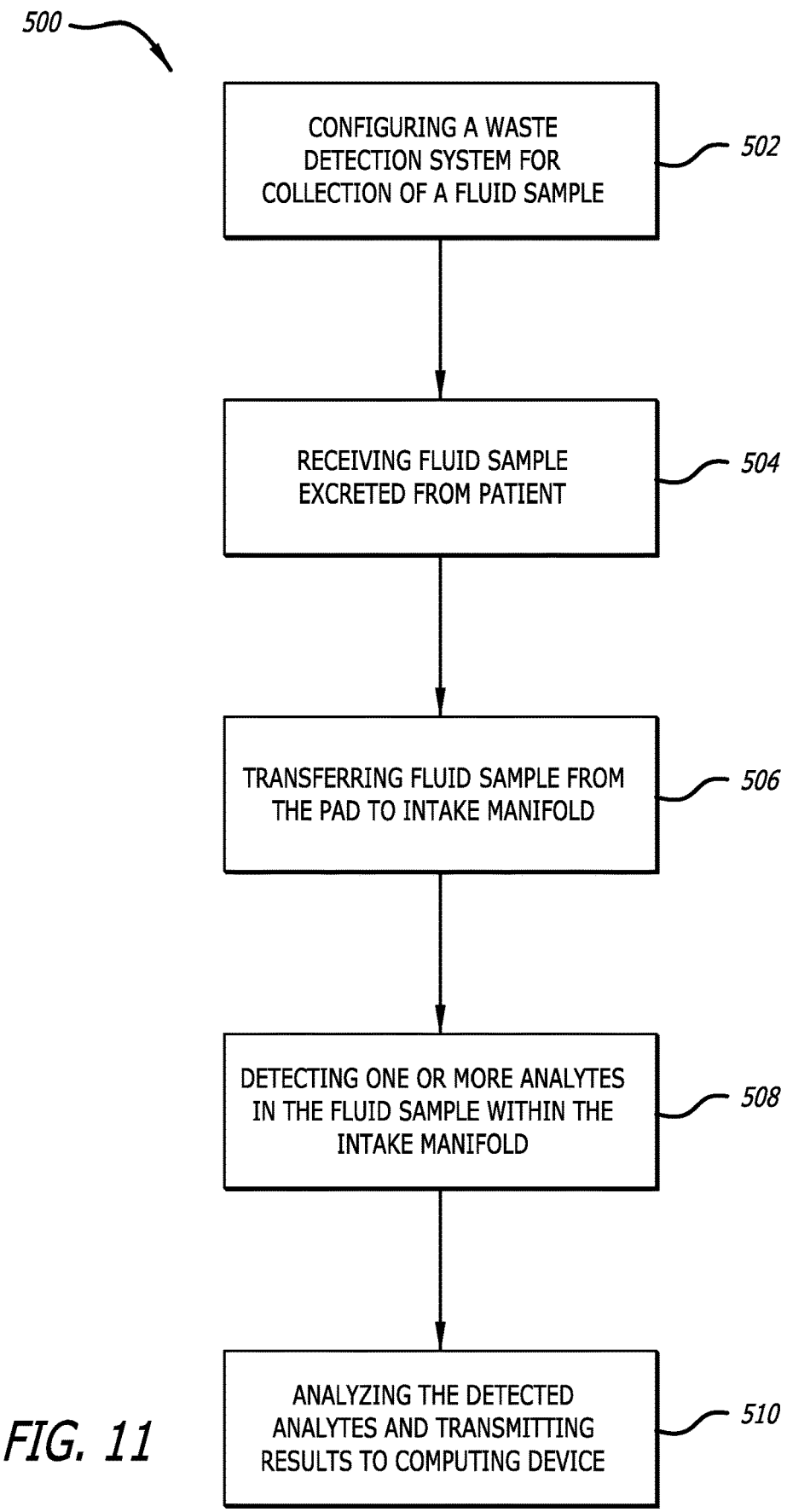
FIG. 11 illustrates a flow chart of an exemplary method of receiving and analyzing a fluid sample excreted from a patient, in accordance with some embodiments

FIG. 11 illustrates a flow chart of an exemplary method 500 of receiving and analyzing a fluid sample excreted from a patient for waste, in accordance with some embodiments. In some embodiments, the method 500 includes configuring the waste detection system 400 for collection of a fluid sample (block 502). In some embodiments, configuring the waste detection system 400 includes placing the pad 410 under the lower abdominal region of a patient. In some embodiments, configuring the waste detection system 400 includes placing the pad 410 on the medical bed 200. In some embodiments, placing the pad 410 on the medical bed 200 includes coupling the pad 410 to the medical bed 200. In some embodiments, configuring the waste detection system 400 includes placing the intake manifold 440 in fluid communication with the pad 410. In some embodiments, placing the intake manifold 440 in fluid communication with the pad 410 includes detachably coupling the intake manifold 440 with the pad 410. In some embodiments, configuring the waste detection system 400 includes activating the analyzer 480.

The method 500 further includes receiving a fluid sample excreted from the patient (block 504). In some embodiments, receiving a fluid sample excreted from the patient includes the pad 410 receiving the fluid sample from the patient. In some embodiments, the pad 410 receiving the fluid sample by absorbing the fluid sample into the pad 410 including into the one or more layers 420.

The method 500 includes transferring the fluid sample from the pad 410 to the intake manifold 440 (block 506). In some embodiments, transferring the fluid sample from the pad 410 to the intake manifold 440 includes the pad 410 using the pad channels 421 to transfer the fluid sample to the one or more microfluidic channels 430 in fluid communication with the intake manifold 440. In some embodiments, transferring the fluid sample from the pad 410 to the intake manifold 440 includes using gravity flow or capillary action.

The method 500 includes detecting one or more analytes in the fluid sample within the intake manifold 440 (block 508). In some embodiments, detecting one or more analytes in the fluid sample includes using the one or more reagents 460 to detect the one or more analytes. In some embodiments, the one or more reagents 460 may emit a visible color or undergo a visible color change when detecting the one or more analytes in the fluid sample within the intake manifold 440. In some embodiments, the one or more analytes in the fluid sample may be above a threshold for the one or more reagents 460 to emit a visible color or undergo a visible color change. In some embodiments, the one or more reagents 460 may emit a visible color or undergo a visible color change in proportion to the concentration of the one or more analytes within the fluid sample. In some embodiments, the one or more analytes may include urine, stool, bacteria, glucose, proteins, or the like. In some embodiments, each chamber 452 in the intake manifold 440 may include separate reagents 460 to detect different analytes or each chamber 452 may include the same reagents 460 to detect the same analytes.

The method 500 further includes analyzing the detected one or more analytes and transmitting the results to the computing device 495 or EMR system (block 510). In some embodiments, analyzing the detected one or more analytes includes the analyzer 480 detecting the visible color or visible color changes. In some embodiments, the analyzer 480 may be configured to detect the visible color or visible color changes within the intake manifold 440 or the removable wafer 454 when the intake manifold 440 or the removable wafer 454 is coupled to the analyzer 480. In some embodiments, the analyzer 480 detects the visible color or visible color changes by a camera 481 capturing one or more images of the intake manifold 440 or the removable wafer 454. In some embodiments, the console 482 may be configured to correlate the detected visible color or visible color changes with a result value and time of day value, as described above. In some embodiments, the result value may be above or below a threshold. In some embodiments, analyzing the detected one or more analytes and transmitting the results to the computing device 495 or the EMR system includes transmitting the results when the analyzer 480 is coupled to the docking station 494. In some embodiments, the analyzer 480 may wireless transmit the results to the computing device 495.

In some embodiments, analyzing and transmitting the results includes the analyzer 480 analyzing the results and transmitting the results to a computing device or an electronic medical records system. In some embodiments, transmitting includes wirelessly transmitting the results from the analyzer to the computing device or the electronic medical records system. In some embodiments, analyzing the results include the analyzer 480 capturing one or more images of the intake manifold 440. In some embodiments, analyzing includes comparing the one or more captured images of the intake manifold 440 to standardized image.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A waste detection system, comprising:
a pad configured to acquire a fluid sample excreted from a patient, the pad having one or more layers and at least one microfluidic channel configured to receive therein the fluid sample; and
an intake manifold detachably coupled to the pad, the intake manifold in fluid communication with the at least one microfluidic channel, the intake manifold configured to receive therein the fluid sample, the intake manifold having one or more reagents therein configured to detect a presence of waste within the fluid sample excreted from the patient.

2. The waste detection system according to claim 1, wherein the one or more layers includes a portion of the one or more layers having absorbent properties.

3. The waste detection system according to claim 2, wherein the one or more microfluidic channels are located within the portion having absorbent properties.

4. The waste detection system according to claim 1, wherein the one or more layers includes a portion of the one or more layers having wicking properties.

5. The waste detection system according to claim 4, wherein the one or more microfluidic channels are located within the portion having wicking properties.

6. The waste detection system according to claim 1, wherein the pad is placed under a lower abdominal region of the patient.

7. The waste detection system according to claim 1, wherein the waste includes urine, stool, blood or *Clostridioides difficile*.

8. The waste detection system according to claim 1, wherein the one or more microfluidic channels are coupled to the intake manifold at a proximal side or a distal side.

9. The waste detection system according to claim 1, wherein the intake manifold includes one or more chambers configured to include the one or more reagents therein.

10. The waste detection system according to claim 9, wherein the one or more chambers are configured in the shape of a cylinder, a rectangular prism, or an inverse cone.

11. The waste detection system according to claim 9, wherein the one or more reagents are in a solution form, a liquid form, or a powder form.

12. The waste detection system according to claim 1, wherein the pad is disposable.

13. The waste detection system according to claim 1, wherein the intake manifold is disposable or reusable.

14. The waste detection system according to claim 1, wherein the intake manifold includes one or more hooks or one or more magnets configured to suspend the intake manifold from a medical bed.

15. The waste detection system according to claim 1, further comprising:
an analyzer configured to receive therein a portion of the intake manifold, the analyzer having a console in communication with a camera configured to detect one or more visible colors or visible color changes of the one or more reagents within the intake manifold.

16. The waste detection system according to claim 15, wherein the one or more reagents are configured to detect a presence of waste within the fluid sample by detecting one or more analytes within the fluid sample.

17. The waste detection system according to claim 16, wherein detecting the one or more analytes within the fluid sample includes detecting the one or more analytes when the one or more analytes are above a threshold.

18. The waste detection system according to claim 16, wherein the one or more analytes detected include a panel of disease state specific analytes or treatment plan specific analytes.

19. The waste detection system according to claim 16, wherein the one or more analytes detected include urine, stool, glucose, protein, or bacteria.

20. The waste detection system according to claim 19, wherein the bacteria includes Clostridium difficile.

21. The waste detection system according to claim 16, wherein the one or more reagents are configured to emit a color or undergo a visible color change in proportion to a concentration of the detected one more analytes detected in the fluid sample.

22. The waste detection system according to claim 15, wherein detecting one or more analytes within the fluid sample includes the one or more reagents emitting a visible color or undergoing a visible color change.

23. The waste detection system according to claim 15, wherein the intake manifold includes one or more chambers configured to receive a portion of the fluid sample therein.

24. The waste detection system according to claim 23, wherein each chamber includes the one or more reagents therein configured to detect different analytes within the fluid sample.

25. The waste detection system according to claim 23, wherein each chamber includes the one or more reagents therein configured to detect same analytes within the fluid sample.

26. The waste detection system according to claim 23, wherein the intake manifold includes a removable wafer, the removable wafer having one or more wafer compartments in fluid communication with the one or more chambers, the one or more wafer compartments configured to receive therein a portion of the fluid sample, the removable wafer including a wafer cover configured to seal therein the fluid sample.

27. The waste detection system according to claim 26, wherein the analyzer is configured to receive the removable wafer therein.

28. The waste detection system according to claim 26, wherein each of the pad, the intake manifold, and the removable wafer are disposable or reusable.

29. The waste detection system according to claim 15, wherein the console includes one or more processors, an energy source, non-transitory computer readable medium, and a plurality of logic modules.

30. The waste detection system according to claim 29, wherein the console is in communication with a docking station, a computing device, or an electronic medical record system.

31. The waste detection system according to claim 30, wherein the plurality of logic modules, when executed by the one or more processors are configured to perform operations including:
  activating the analyzer including the camera;
  calibrating the analyzer including the camera;
  capturing one or more images of the intake manifold or a removable wafer;
  detecting one or more colors or color changes from the one or more images of the intake manifold or the removable wafer;
  correlating the one or more colors or color changes detected with a result value and a time of day value;
  analyzing the result value; and
  transmitting the result value, the time of day value and the captured one or more images to a computing device or an electronic medical record system.

32. The waste detection system according to claim 31, wherein calibrating the analyzer includes calibrating the analyzer with a reference color pad.

33. The waste detection system according to claim 31, wherein capturing one or more images of the intake manifold or the removable wafer includes the camera capturing the one or more images when the intake manifold or the removable wafer is coupled to the analyzer.

34. The waste detection system according to claim 30, wherein the analyzer is configured to detachably couple to the docking station.

35. The waste detection system according to claim 15, wherein the pad includes pad channels in fluid communication with the one or more microfluidic channels, the pad channels defined by absorbent material between wicking fiber.

36. The waste detection system according to claim 35, wherein a portion of the wicking fiber or an entirety of the wicking fiber is covered with a hydrophilic coating configured to create a hydrophilic gradient.

37. A waste detection system, comprising:
  a pad configured to acquire a fluid sample excreted from a patient, the pad having one or more layers and at least one microfluidic channel configured to receive therein the fluid sample; and
  an intake manifold in fluid communication with the at least one microfluidic channel, the intake manifold configured to receive therein the fluid sample, the intake manifold having one or more reagents therein configured to detect a presence of waste within the fluid sample excreted from the patient, wherein the intake manifold includes one or more hooks or one or more magnets configured to suspend the intake manifold from a medical bed.

* * * * *